United States Patent
Aravamudhan et al.

(10) Patent No.: US 11,208,647 B2
(45) Date of Patent: Dec. 28, 2021

(54) APPLICATION OF ELECTRICAL STIMULATION VIA NANOELECTRODES TO MODULATE STEM CELLS

(71) Applicant: North Carolina Agricultural and Technical State University, Greensboro, NC (US)

(72) Inventors: Shyam Aravamudhan, Oak Ridge, NC (US); Komal Garde, Santa Clara, CA (US)

(73) Assignee: North Carolina Agricultural and Technical State University, Greensboro, NC (US)

( * ) Notice: Subject to any disclaimer, the term of this patent is extended or adjusted under 35 U.S.C. 154(b) by 189 days.

(21) Appl. No.: 16/423,913

(22) Filed: May 28, 2019

(65) Prior Publication Data
US 2019/0359967 A1 Nov. 28, 2019

Related U.S. Application Data

(60) Provisional application No. 62/676,423, filed on May 25, 2018.

(51) Int. Cl.
*C12N 13/00* (2006.01)
*C12N 5/0793* (2010.01)

(52) U.S. Cl.
CPC ........... *C12N 13/00* (2013.01); *C12N 5/0619* (2013.01); *C12N 2506/1384* (2013.01); *C12N 2529/00* (2013.01)

(58) Field of Classification Search
None
See application file for complete search history.

(56) References Cited

PUBLICATIONS

Garde, Komal S; et al; "Nanoelectrodes to Differentiate Adipose Derived Stem Cells into Neural Lineage" Proceedings of the 17th IEEE International Conference on Nanotechnology, Pittsburgh, PA, Jul. 25-28, 2017 (Year: 2017).*
Gimble et al., "Adipose-derived stem cells for regenerative medicine," Circulation research, 100(9), pp. 1249-1260 (2007).
Garde & Aravamudhan, "Penetrating nanoelectrodes for Stimulation of Cells," ECS Transactions, vol. 77, No. 11, pp. 1701-1709 (2017).
Hai et al., "In-cell recordings by extracellular microelectrodes," Nature methods, 7(3), p. 200 (2010).
Hanson et al., "Characterization of the cell-nanopillar interface by transmission electron microscopy," Nano letters, 12(11), pp. 5815-5820 (2012).
Heo et al., "Directly induced neural differentiation of human adipose-derived stem cells using three-dimensional culture system of conductive microwell with electrical stimulation," Tissue Engineering Part A, 24(7-8), pp. 537-545 (2018).
Hronik-Tupaj & Kaplan, "A review of the responses of two- and three-dimensional engineered tissues to electric fields," Tissue Engineering Part B: Reviews, 18(3), pp. 167-180 (2012).
Jaatinen et al., "The combination of electric current and copper promotes neuronal differentiation of adipose-derived stem cells," Annals of biomedical engineering, 43(4), pp. 1014-1023 (2015).
Kwak et al., "Interfacing inorganic nanowire arrays and living cells for cellular function analysis," Small, 11(42), pp. 5600-5610 (2015).
Lee et al., "Nondestructive Real-Time Monitoring of Enhanced Stem Cell Differentiation Using a Graphene-Au Hybrid Nanoelectrode Array," Advanced Materials, 30(39), 1802762 (2018).
Lin et al., "Accurate nanoelectrode recording of human pluripotent stem cell-derived cardiomyocytes for assaying drugs and modeling disease," Microsystems & nanoengineering, 3(1), pp. 1-7 (2017).
Neuhuber et al., "Reevaluation of in vitro differentiation protocols for bone marrow stromal cells: disruption of actin cytoskeleton induces rapid morphological changes and mimics neuronal phenotype," Journal of neuroscience research, 77(2), pp. 192-204 (2004).
Pavesi et al., "Electrical conditioning of adipose-derived stem cells in a multi-chamber culture platform," Biotechnology and bioengineering, 111(7), pp. 1452-1463 (2014).
Robinson et al., "Vertical nanowire electrode arrays as a scalable platform for intracellular interfacing to neuronal circuits," Nature nanotechnology, 7(3), pp. 180-184 (2012).
Thrivikraman et al., "Electrically driven intracellular and extracellular nanomanipulators evoke neurogenic/cardiomyogenic differentiation in human mesenchymal stem cells," Biomaterials, 77, 26-43 (2016).
Thrivikraman et al., "Intermittent electrical stimuli for guidance of human mesenchymal stem cell lineage commitment towards neural-like cells on electroconductive substrates," Biomaterials, 35(24), 6219-6235 (2014).

\* cited by examiner

*Primary Examiner* — David W Berke-Schlessel
(74) *Attorney, Agent, or Firm* — Jenkin, Wilson, Taylor & Hunt, P.A.

(57) ABSTRACT

The presently disclosed subject matter relates generally to the delivery of electrical stimuli via cell-penetrating nanoelectrodes. Such electrical stimuli leads to differentiation of cells, including but not limited to adipose derived stem cells, to neural lineage, specifically to neural cells.

16 Claims, 9 Drawing Sheets

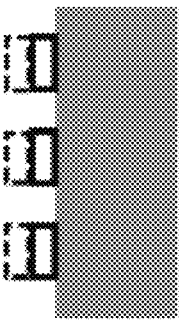
FIG. 1A
FIG. 1B
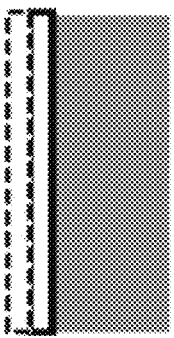
FIG. 1C
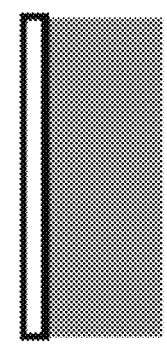
FIG. 1D
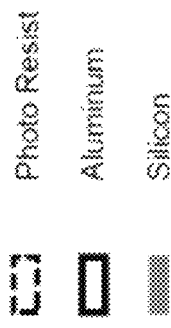
FIG. 1E
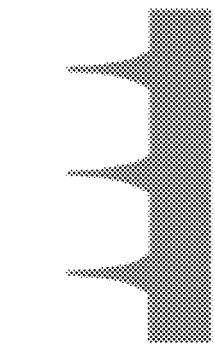
FIG. 1F
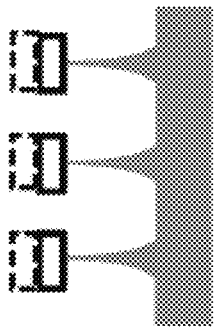
FIG. 1G
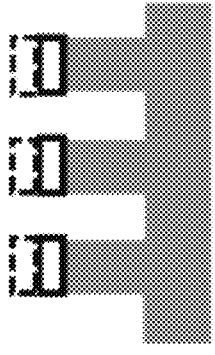

APPLICATION OF ELECTRICAL STIMULATION VIA NANOELECTRODES TO MODULATE STEM CELLS

RELATED APPLICATIONS

The presently disclosed subject matter claims the benefit of U.S. Provisional Patent Application Ser. No. 62/676,423 filed May 25, 2018; the disclosure of which is incorporated herein by reference in its entirety.

TECHNICAL FIELD

The presently disclosed subject matter relates generally to the delivery of electrical stimuli via cell-penetrating nanoelectrodes. Such intracellular stimuli can lead to differentiation of stem cells, including but not limited to Adipose Derived Stem Cells (ADSCs), to neural lineage, specifically to neural cells.

BACKGROUND

Regenerative medicine, using tissues derived from stem cells, requires consistent, high quality, and scalable production of stem cells. ADSCs have gained increasing attention for applications related to regenerative medicine and tissue engineering due to their high proliferative capacity, multi-lineage potential and ease in harvesting compared to other stem cells.

A variety of methods have been identified for ADSC differentiation, including serum free induction using growth factors, chemical induction or even spontaneous differentiation with no intervention has been employed. In some examples, additives employed in cell differentiation lead to problems in translational studies, to cell toxicity and to induced cell stress.

A controlled method to differentiate ADSC in the absence of biological or chemical factors, with individual control over stem cell differentiation, has not been established.

SUMMARY

In some embodiments, the presently disclosed subject matter provides a method of modulating an adipose-derived stem cell having a cytosol, comprising exposing said cytosol to electrical stimulation, thereby modulating the cell, wherein a nanoelectrode provides said electrical stimulation. In some embodiments, modulating comprises differentiating the cell to a neural lineage, optionally to a neural cell. In some embodiments, the differentiation to neural lineage is characterized by an increase in one or more neural stem cell markers, such as, one or more of Vimentin, Nestin, and PAX6. In some embodiments, the differentiation to neural lineage is characterized by a decrease in one or more adipose derived stem cells markers, such as one or more of CD9, CD10, CD13, CD29, CD44, CD49, CD54, CD55, CD59, CD73, CD90, CD105, CD106, CD146, CD166, ASMA, Collagen-1, Endomucin, and Fibronectin. In some embodiments, CD29 and/or CD44 is decreased. In some embodiments, the nanoelectrode penetrates the cell and is in physical contact with the cytosol. In some embodiments, the electrical stimulation is pulsed direct current between about 50 mV/cm and 500 mV/cm field strength. In some embodiments, the stimulation is a monophasic 100 ms square pulse at 1 Hz frequency.

In some embodiments, the cell is exposed to a growth factor or chemical agent, whereby said modulating comprises differentiating the cell to a neural lineage and said differentiating occurs in a shorter time compared to differentiating in the absence of said electrical stimulation. In other embodiments, the cell is not exposed to a growth factor or chemical agent during said modulation.

In some embodiments, the presently disclosed subject matter provides a method for differentiating an adipose-derived stem cell to a neural cell comprising applying electrical stimulation to the cytosol of the stem cell, wherein a nanoelectrode provides said electrical stimulation to the cytosol. In some embodiments, the nanoelectrode penetrates the cell and is in physical contact with the cytosol. In some variations, the electrical stimulation is pulsed direct current between about 50 mV/cm and 500 mV/cm field strength.

In some variations of any aspect or embodiment, the nanoelectrode is a nanofin having a width of no more than about 300 nm and a length of no more than about 10 µm. In other variations, the nanoelectrode is a conical nanopillar having a radius no larger than about 300 nm.

An objective of the presently disclosed subject matter having been stated hereinabove, and which is achieved in whole or in part by the presently disclosed subject matter, other objectives will become evident as the description proceeds when taken in connection with the accompanying drawings as best described herein below.

BRIEF DESCRIPTION OF THE DRAWINGS

It will be understood that the drawings are for the purpose of describing embodiments of the inventions and are not intended to limit the inventions thereto.

FIG. 1A is a schematic drawing showing a step in a process for nanoelectrode fabrication wherein an aluminum layer is deposited on a silicon substrate.

FIG. 1B is a schematic drawing showing a step in a process for nanoelectrode fabrication where a spin photoresist layer is deposited on the aluminum deposited in FIG. 1A.

FIG. 1C is a schematic drawing showing a step in a process for nanoelectrode fabrication where the photoresist layer from FIG. 1B is exposed and developed to form a pattern.

FIG. 1D is a schematic drawing showing a step in the process for nanoelectrode fabrication wherein the aluminum layer exposed after exposure and development of the photoresist is etched.

FIG. 1E is a schematic drawing showing a step in the process for nanoelectrode fabrication wherein the silicon substrate is subjected to anisotropic etching.

FIG. 1F is a schematic drawing showing a step in the process for nanoelectrode fabrication wherein the silicon substrate is subjected to isotropic etching.

FIG. 1G is a schematic drawing showing a step in the process for nanoelectrode fabrication wherein the photoresist and aluminum are removed from the etched silicon substrate.

DETAILED DESCRIPTION

Figure 2C:
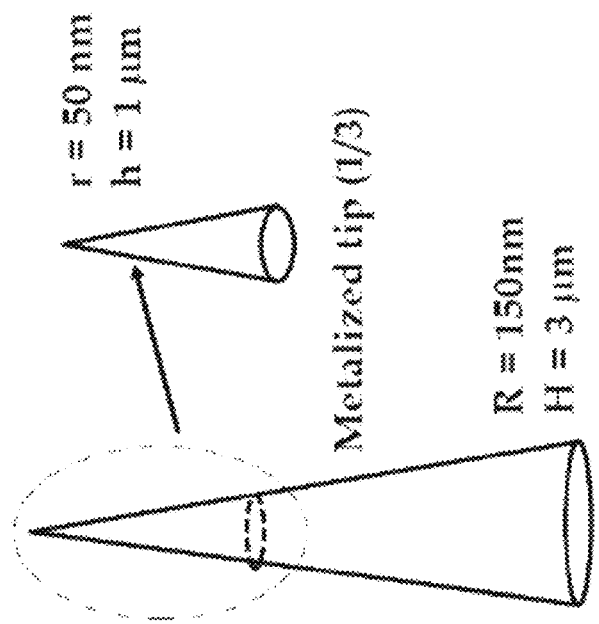
FIG. 2C is a 3-dimensional representation of a single conical nanopillar showing the dimensions of the metalized tip.

The presently disclosed subject matter will now be described more fully. The presently disclosed subject matter can, however, be embodied in different forms and should not be construed as limited to the embodiments set forth herein below and in the accompanying Examples. For example, features illustrated with respect to one embodiment can be incorporated into other embodiments, and features illustrated with respect to a particular embodiment can be deleted from that embodiment. Thus, one or more of the method steps included in a particular method described herein can, in other embodiments, be omitted and/or performed independently. In addition, numerous variations and additions to the embodiments suggested herein, which do not depart from the instant invention, will be apparent to those skilled in the art in light of the instant disclosure. Hence, the following description is intended to illustrate some particular embodiments of the invention, and not to exhaustively specify all permutations, combinations and variations thereof. It should therefore be appreciated that the present invention is not limited to the particular embodiments set forth herein. Rather, these particular embodiments are provided so that this disclosure will more clearly convey the full scope of the invention to those skilled in the art.

All references listed herein, including but not limited to all patents, patent applications and publications thereof, and scientific journal articles, are incorporated herein by reference in their entireties to the extent that they supplement, explain, provide a background for, or teach methodology, techniques, and/or compositions employed herein.

Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. References to techniques employed herein are intended to refer to the techniques as commonly understood in the art, including variations on those techniques or substitutions of equivalent techniques that would be apparent to one of skill in the art.

Following long-standing patent law convention, the terms "a", "an", and "the" refer to "one or more" when used in this application, including the claims.

The term "and/or" when used in describing two or more items or conditions, refers to situations where all named items or conditions are present or applicable, or to situations wherein only one (or less than all) of the items or conditions is present or applicable.

The use of the term "or" in the claims is used to mean "and/or" unless explicitly indicated to refer to alternatives only or the alternatives are mutually exclusive, although the disclosure supports a definition that refers to only alternatives and "and/or."

As used herein "another" can mean at least a second or more.

As used herein, the term "about", when referring to a value is meant to encompass variations of in one example ±20% or ±10%, in another example ±5%, in another example ±1%, and in still another example ±0.1% from the specified amount, as such variations are appropriate to perform the disclosed methods.

As used herein, "neural cells" refers to the nerve-like cells including neurons, astrocytes, and microglias, as part of the peripheral nervous system or the central nervous system.

As used herein, differentiating to a "neural lineage" refers to a cell that becomes partially or fully committed to a specific neural phenotype of the peripheral nervous system or the central nervous system.

As used herein "NSC markers" or "neural stem cell markers" refer to PAX6, Nestin and Vimentin. These markers typically increase as a cell, such as ADSC, is differentiated to neural lineage.

As used herein "Vimentin" refers a type III intermediate filament protein that is expressed in glial cells, namely, oligodendrocytes, microglia or astrocytes and neuronal precursors.

As used herein, "Nestin" refers to a type VI intermediate filament protein that is expressed in mesenchymal cells. Nestin is required for the survival of neural progenitor cells.

As used herein, "PAX6" refers to paired box 6, which plays a pivotal role in the neuronal fate determination and neural stem cell proliferation. PAX genes encode nuclear transcription factors which are main controllers of developmental processes.

As used herein, "ADSC markers" or "adipose-derived stem cell markers" refer to positive markers CD29 and CD44 as well as a negative marker, CD45. Positive cellular markers and genes for ADSC further include CD9, CD10, CD13, CD49, CD54, CD55, CD59, CD73, CD90, CD105, CD106, CD146, CD166, ASMA, Collagen-1, Endomucin, and Fibronectin. Negative cellular markers and genes for ADSC further include CD11b, CD14, CD19, CD31, CD34, CD79a, CD80, CD177, CD133, CD144, HLA-DR, HLA II, c-Kit, Lin, MyoD88, and STRO-1.

As used herein "ADSC" or "adipose-derived stem cells" refer to stem cells derived from adipose tissues. ADSC are mesenchymal stem cells derived from adipose tissues.

As used herein "adipose" refers to any type of fat tissue. The adipose tissue is optionally brown or white adipose tissue, derived from subcutaneous, omental/visceral, mammary, gonadal, or other adipose tissue site. The adipose can be subcutaneous white adipose tissue. Such cells include both a primary cell culture and an immortalized cell line. The adipose tissue can be from any organism having fat tissue. In one embodiment, the adipose tissue is mammalian, such human adipose tissue. One source of adipose tissue is liposuction surgery; a variety of methods to isolate ADSC from adipose tissue is known to those of skill in the art. The source of adipose tissue or the method of extraction of adipose tissue can be any known to those of skill in the art. Alternately, ADSC can be purchased commercially.

As used herein, "cytosol" refers to the aqueous component of the cytoplasm of a cell, within which various organelles and particles are suspended.

As used herein, 'growth factors" refers to a naturally occurring substance capable of stimulating cellular differentiation and as generally defined, include cytokines and hormones; growth factors are also capable of stimulating cellular growth, proliferation, and healing. Growth factors include, but are not limited to, fibroblast growth factor-2, epidermal growth factor, platelet derived growth factor, transforming growth factor, basic fibroblast growth factor, nerve growth factor, insulin-like growth factor-1, and brain-derived neurotrophic factor.

As used herein, "chemical agents" refer to chemicals which induce changes to stem cells towards neural lineage, including but not limited to butylated hydroxyanisole, dimethyl sulfoxide, 2-mercaptoethanol, tretinoin, indomethacin and 3-isobutyl-1-methylxanthine. As used herein, "chemical agents" can additionally include metals, optionally in the form of nanoparticles, which facilitate the induction of stem cells towards neural lineage; such metals and/or nanoparticles include copper and gold.

Figure 2B:
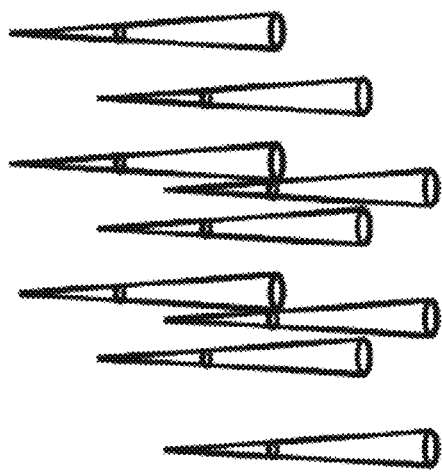
FIG. 2B is a 3-dimensional representation of a nanopillar array, showing the conical nature of the nanopillars.
Figure 2A:
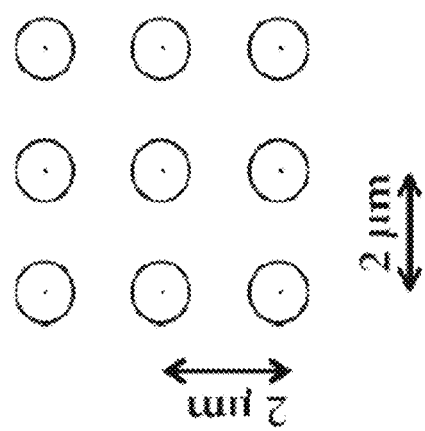
FIG. 2A is a representation of the top view of a 3×3 nanopillar array at spacing of about 2 µm between nanopillars.
Figure 3C:
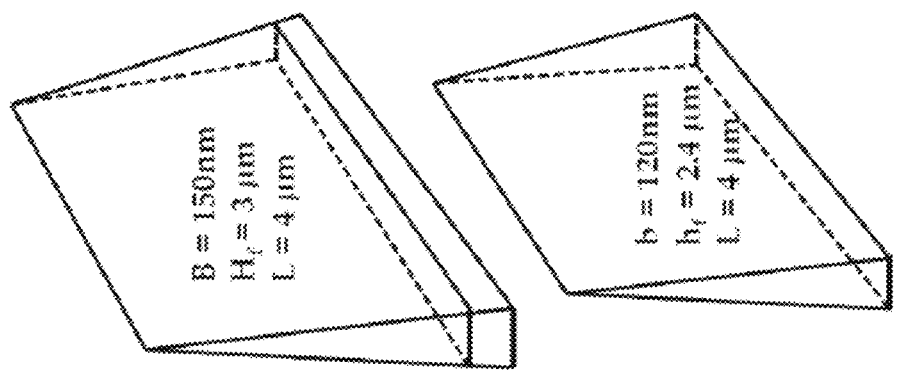
FIG. 3C is a 3-dimensional representation of two nanofins, each with a length of about 4 µm.
Figure 3B:
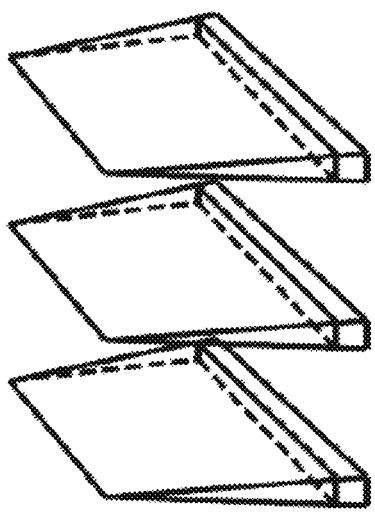
FIG. 3B is a 3-dimensional representation of a nanofin array.
Figure 3A:
FIG. 3A is a representation of the top view of a 3×1 nanofin array.
Figure 3A:
Figure 3A:
Figure 3A:
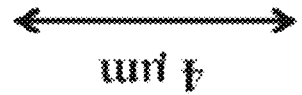

As used herein, "nanoelectrode" refers to a solid electric conductor that carries electric current into non-metallic solids or liquids, such as a cell. As disclosed herein, nanoelectrodes are typically no more than about 25 μm in height and no more than about 10 μm in length. As exemplified herein, nanoelectrodes can be nanopillars or nanofins, typically prepared using nanolithography. Nanopillars, as described herein, are conical nanopillars (FIG. 2). Nanopillars typically have a metalized tip comprising the top third of the pillar. In the samples prepared here, the total metallized surface of a pillar was typically about 1.4 μm$^2$, but other surface areas can be prepared using a variety of methods, including nanolithography. In one example, a 3×3 array was chosen with a pitch of 2 μm in another example, spacing between the nanofins was about 9-11 μm. Preparation of different patterns can be used. Nanopillars showed reduced electrode impedance while maintaining minimal cell damage. Nanofins, as disclosed herein, typically have a metallized tip comprising the top four-fifths of the fin (FIGS. 3A-3C). In the samples prepared here, the total metallized surface of a fin was typically about 58.5 μm$^2$, but other surface areas can be prepared using a variety of methods, including nanolithography. The nanofins disclosed herein provided a larger capacitance and smaller charge transfer resistance compared to the nanopillars of the present application. In one example, a 3×1 array was chosen with a pitch of 2 μm; in another example, spacing between the nanofins was about 9-11 μm. Preparation of different patterns can be used. Two types of nanofins were exemplified herein. Nanofins-i had tip dimensions of ~100 nm×3 μm, a height of ~8-10 interpillar distances of ~15×11 μm and a density of 60.6×10$^3$ fins/cm$^2$. Nanofins-ii had tip dimensions of ~100 nm×7.5 μm, a height of ~8-10 μm, inter-electrode distances of ~13×11 μm and a density of 4.8×10$^3$ fins/cm$^2$. Variations of these dimensions and different nanoelectrode shapes can be readily identified by those of skill in the art to achieve physical contact with the ADSC cytosol, i.e. the penetration of the cell by the nanoelectrode.

In some embodiments, the presently disclosed subject matter provides a method of modulating an adipose-derived stem cell having a cytosol, comprising exposing said cytosol to electrical stimulation, thereby modulating the cell, wherein a nanoelectrode provides said electrical stimulation. In some embodiments, modulating comprises differentiating the cell to a neural lineage, in some embodiments, modulating comprises differentiating the cell to a neural cell.

In some embodiments, the presently disclosed subject matter provides a method for differentiating an adipose-derived stem cell to a neural cell comprising applying electrical stimulation to the cytosol of the stem cell, wherein a nanoelectrode provides said electrical stimulation to the cytosol.

In some embodiments, the nanoelectrode penetrates the cell and is in physical contact with the cytosol.

In some embodiments, differentiating to neural lineage or neural cell is characterized by an increase in one or more neural stem cell markers, such as, one or more of Vimentin, Nestin, and PAX6. In some embodiments, differentiating to neural lineage or neural cell is characterized by a decrease in one or more adipose derived stem cells markers, such as one or more of CD9, CD10, CD13, CD29, CD44, CD49, CD54, CD55, CD59, CD73, CD90, CD105, CD106, CD146, CD166, ASMA, Collagen-1, Endomucin, and Fibronectin. In some embodiments, CD29 and/or CD44 is decreased.

In some variations of any aspect or embodiment, the electrical stimulation is pulsed direct current between about 50 mV/cm and 500 mV/cm field strength. Alternately, the field strength is between about 100 mV/cm and 250 mV/cm, or between about 150 mV/cm and 200 mV/cm. In some embodiments, the electrical stimulation is no more than about 50 mV/cm, no more than about 100 mV/cm, no more than about 150 mV/cm, no more than about 200 mV/cm, no more than about 200 mV/cm, no more than about 250 mV/cm, no more than about 300 mV/cm, no more than about 350 mV/cm, no more than about 400 mV/cm, no more than about 450 mV/cm, no more than about 500 mV/cm, no more than about 550 mV/cm, no more than about 600 mV/cm, no more than about 650 mV/cm, no more than about 700 mV/cm, or no more than about 750 mV/cm In some embodiments, the stimulation is a monophasic 100 ms square pulse at 1 Hz frequency. In some embodiments, the period of stimulation is no more than about 5 minutes; alternately, the period of stimulation is no more than about 10 minutes, no more than about 15 minutes, no more than about 20 minutes, no more than about 25 minutes, no more than about 30 minutes, no more than about 35 minutes, no more than about 40 minutes, no more than about 45 minutes, no more than about 50 minutes, no more than about 55 minutes, or no more than about 60 minutes. In some embodiments, the cells are exposed to electrical stimulation for a window of time on no more than about 2 days; alternately, the cells are exposed to electrical stimulation for a window of time on no more than about 3 days, no more than about 4 days, no more than about 5 days, no more than about 6 days, no more than about 7 days, no more than about 8 days, no more than about 9 days, no more than about 10 days, no more than about 11 days, no more than about 12 days, no more than about 13 days, or no more than about 14 days.

In some variations of any aspect or embodiment, the cell is exposed to a growth factor or chemical agent, whereby said modulating comprises differentiating the cell to a neural lineage and said differentiating occurs in a shorter time compared to differentiating in the absence of said electrical stimulation. In other embodiments, the cell is not exposed to a growth factor or chemical agent during said modulation.

In some variations of any aspect or embodiment, the nanoelectrode is a nanofin having a width of no more than about 300 nm and a length of no more than about 10 µm. In other variations, the nanoelectrode is a conical nanopillar having a radius no larger than about 300 nm.

In one embodiment, the nanoelectrode has a height of no more than about 25 µm, no more than about 20 µm, no more than about 15 µm, no more than about 10 µm, or no more than about 5 µm.

In some embodiments, the nanoelectrode is a nanofin. In some variations, the nanofin has a length of no more than about 10 µm, no more than about 9 µm, no more than about 8 µm, no more than about 7 µm, no more than about 6 µm, no more than about 5 µm, no more than about 4 µm, no more than about 3 µm, no more than about 2 µm or no more than about 1 µm. In one embodiment, the nanofin has a width of no more than about 500 nm, no more than about 400 nm, no more than about 300 nm, no more than about 200 nm, or no more than about 100 nm.

In some embodiments, the nanoelectrode is a nanopillar. In some variations, the nanopillar has a radius of no more than about 500 nm, no more than about 450 nm, no more than about 400 nm, no more than about 350 nm, no more than about 300 nm, no more than about 250 nm, no more than about 200 nm, no more than about 150 nm, no more than about 100 nm, or no more than about 50 nm.

Typically, the extent of electrical stimulus delivered by electrodes depends on the contact area. The placement of the electrode can also affect the amount of signal. The penetrating nanoelectrodes disclosed herein form a tight seal with the penetrated cells and little or no leakage of signal was observed. As shown herein, penetrating nanoelectrodes can interface with or access the interior of a cell without causing cellular damage.

In some embodiments, the presently disclosed subject matter provides high aspect ratio nanoelectrodes, which can be used to stimulate cells via penetration and electrical signals without loss of cellular function. Electrical stimulus applied via the penetrating nanoelectrodes is shown to have differentiated ADSCs into neuronal lineages. Such differentiation can be accomplished without the use of growth factors, genetic manipulators, and/or chemical reagents. Alternately, electrical stimulation via the penetrating nanoelectrodes of the present application can be used in combination with growth factors, genetic manipulators, and/or chemical agents to accelerate the differentiation of the ADSCs into neuronal lineages or neural cells, as compared to the use of such factors, manipulators, or agents on their own.

As disclosed herein, fabrication of nanoelectrodes of the present application builds on silicon on insulator (SOI) substrate, followed by a series of lithographic patterning, deposition and etching steps including focused ion beam (FIB) ion-milling. After surface functionalization with silane coupling (uncoated Si) or thiol chemistry (Au nanoelectrodes), cells were directly cultured/pipetted on the nanoelectrodes.

For cell differentiation, pulsed DC stimuli with monophasic 100 ms square pulse of 100 mV/cm field strength and 1 Hz frequency was applied. No loss of cellular function was observed while the nanoelectrodes accessed the interior of the cells' cytosol.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Nanoelectrode Design and Fabrication

The nanoelectrodes, e.g. the nanopillars and nanofins described in Table 1, were designed to reduce both interfacial impedance and electrode resistance, while maintaining a large seal resistance. For a given area, the nanofins provide a larger electrode surface area compared to nanopillars, and offer advantages with respect to cell-electrode interaction.

The silicon nanoelectrodes were fabricated from a single crystal silicon wafer (University Wafer, Inc., South Boston, Mass.) by standard top-down microfabrication process steps, as shown in FIGS. 1A-1G. The dimensions of the nanoelectrodes were chosen to give desired height, width and thickness at the tip. The density of the nanoelectrodes varied between $4.8 \times 10^3$ and $8.3 \times 10^3$ electrodes/cm$^2$, and the tip dimensions ranged from 100 nm by 100 nm (nanopillars) to 100 nm by 7.5 µm (nanofins).

TABLE I

| Nanoelectrode dimensions. | | | |
|---|---|---|---|
| | Nanopillar | Nanofin-i | Nanofin-ii |
| Tip Dimension | ~100 nm × 100 nm | ~100 nm × 3 µm | ~100 nm × 7.5 µm |
| Height | ~5-6 µm | ~5-6 µm | ~5-6 µm |
| Interpillar distance | ~11 × 11 µm | ~15 × 11 µm | ~19 × 11 µm |
| Density | 8.3 × 10$^3$ pillars/cm$^2$ | 60.6 × 10$^3$ fins/cm$^2$ | 4.8 × 10$^3$ fins/cm$^2$ |

To fabricate the nanoelectrodes, one-sided polished p-type 4-inch silicon wafers were cleaned with acetone and isopropyl alcohol, then a thin layer of aluminum (60-90 nm) was deposited by electron beam deposition technique (FIG. 1A). Positive photoresist S1813 (MICROPOSIT™ S1813™ POSITIVE PHOTORESIST, Rohm and Haas Electronic Materials, Marlborough, Mass.) was then spin-coated onto the wafer (FIG. 1B) typically to a thickness between about 0.5 µm and 2 µm. The wafer was soft baked at 100° C. for one minute, photo-exposed and developed in MF-321 (MICROPOSIT MF-321 DEVELOPER (Shipley Company, Marlborough, Mass.) for 30 seconds (FIG. 1C). The undesired aluminum was then removed using an aluminum etchant—Type A (Transene Company, Inc., Danvers, Mass.)

for two minutes at room temperature (FIG. 1D). The mask pattern yielded a 13 5 mm×5 mm nanoelectrode array on a standard 4-inch wafer.

Figure 4A:
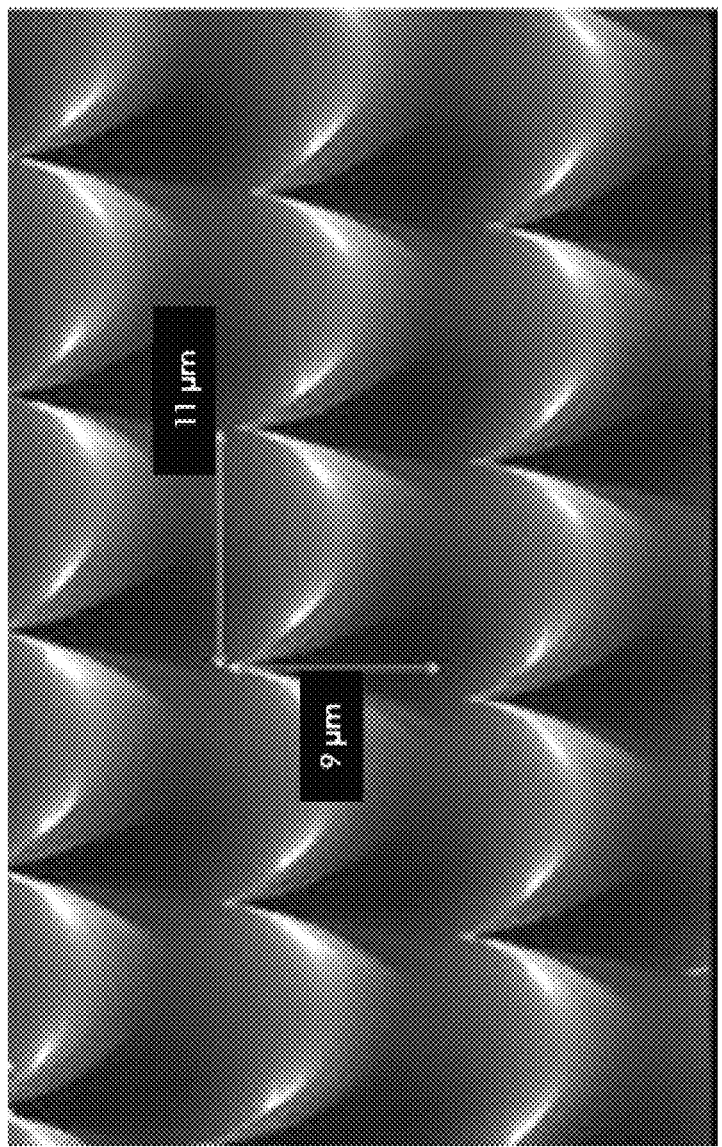
FIG. 4A is a scanning electron micrograph (SEM) image of fabricated conical nanopillar electrodes. The nanopillars have a spacing of 9 µm×11 µm.
Figure 4B:
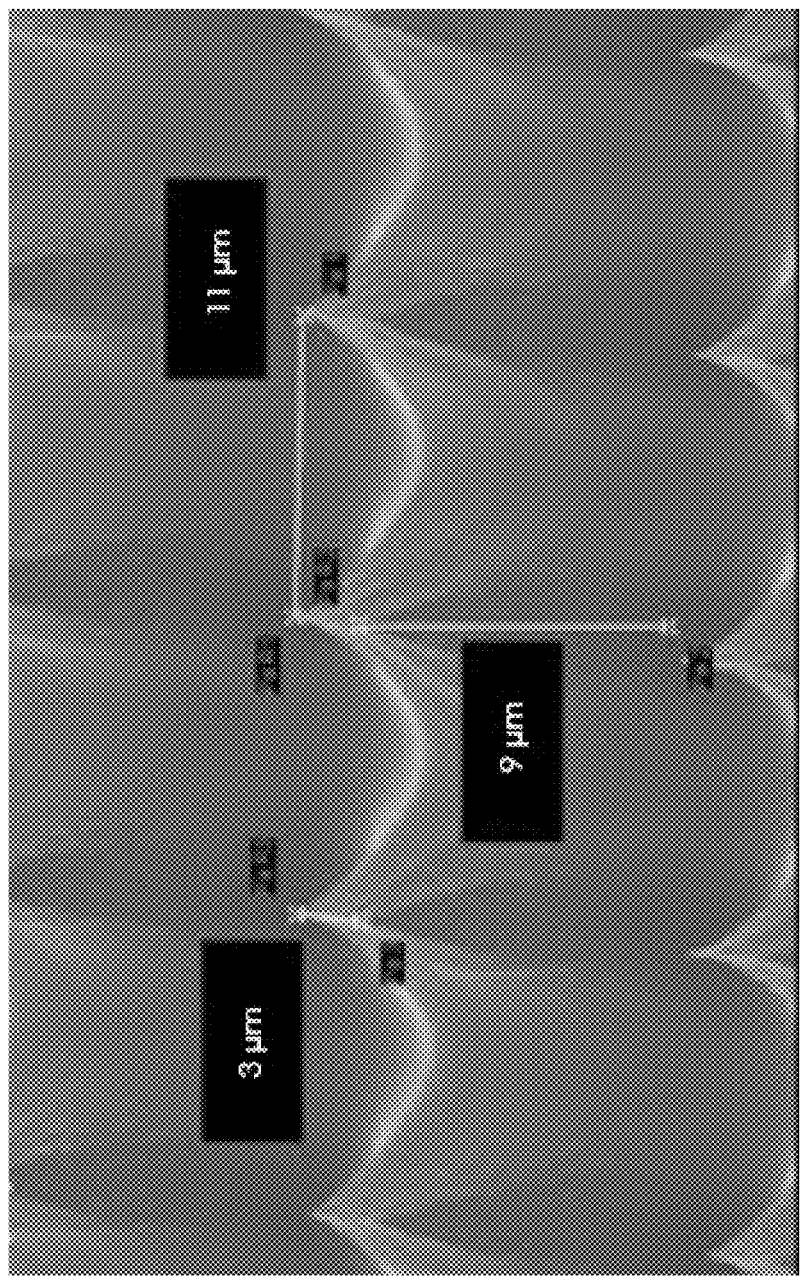
FIG. 4B is an SEM image of fabricated nanofins electrodes, designated herein 'nanofins-I,' about 3 µm in length at a spacing of 9 µm×11 µm.
Figure 4C:
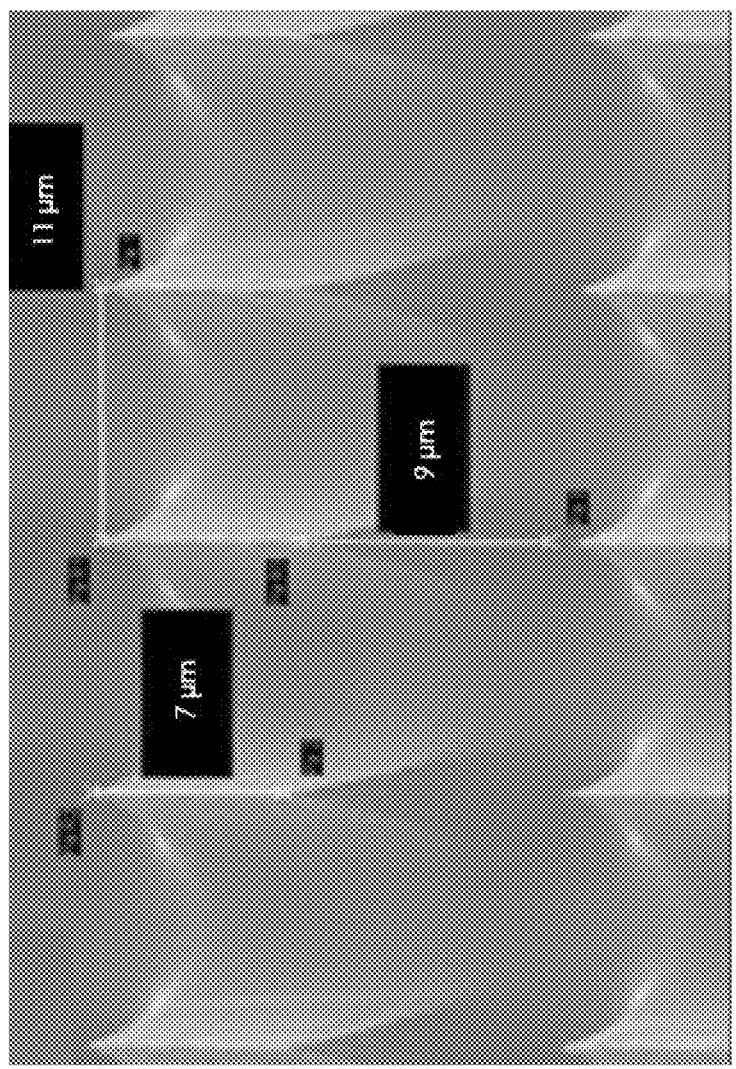
FIG. 4C is an SEM image of fabricated nanofins electrodes, designated 'nanofins-ii,' about 7 µm in length at a spacing of 9 µm×11 µm.
Figure 5B:
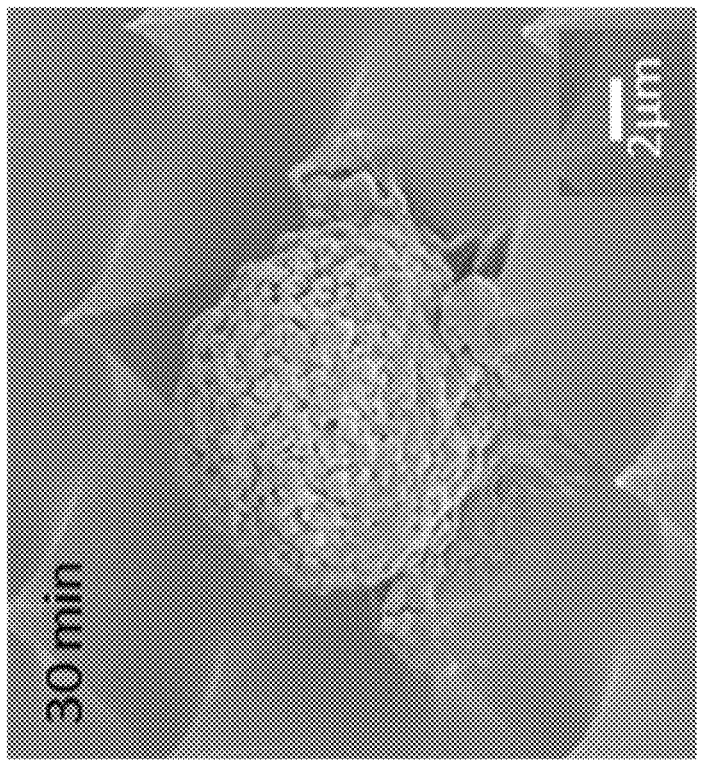
FIG. 5B is an SEM image showing NIH-3T3 cells after 30 minutes on the nanopillar electrode array. The scale bar in the lower right represents 2 µm.
Figure 5A:
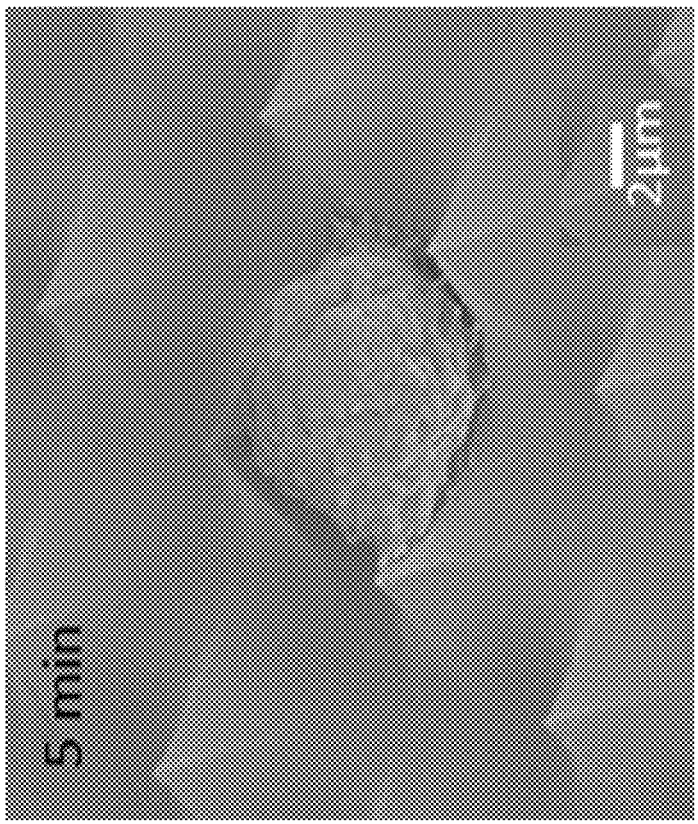
FIG. 5A is an SEM image showing NIH-3T3 cells after 5 minutes on a nanopillar electrode array (wherein the nanopillar electrodes are 100-200 nm in tip diameter and 4-5 µm high, at a density of $8\times10^3$ nanopillars/cm$^2$). The scale bar in the lower right represents 2 µm.
Figure 5D:
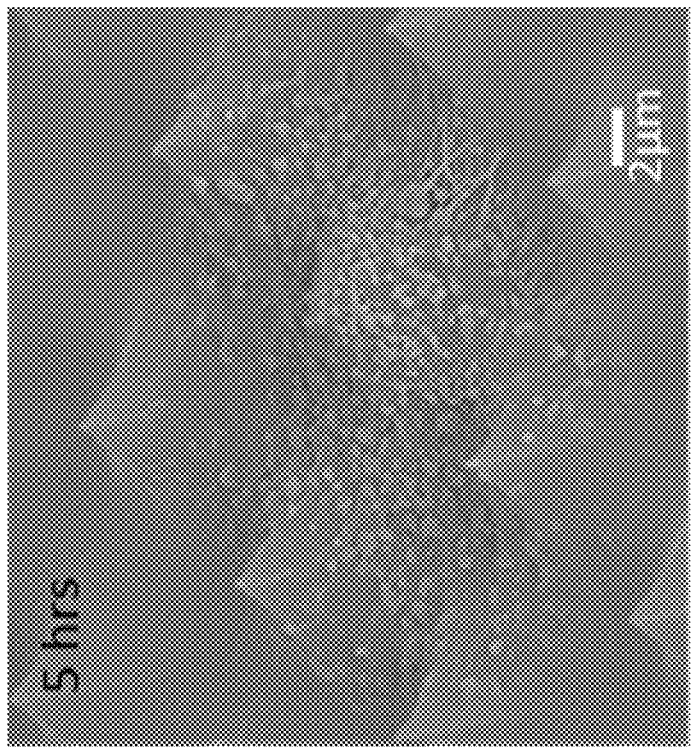
FIG. 5D is an SEM image showing NIH-3T3 cells after 5 hours on the nanopillar electrode array. The scale bar in the lower right represents 2 µm.
Figure 5C:
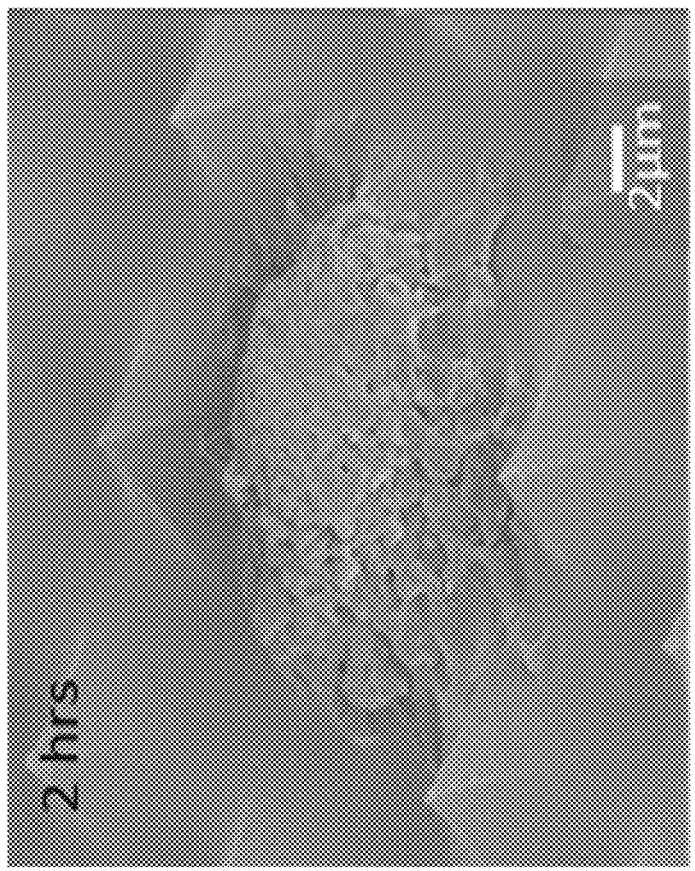
FIG. 5C is an SEM image showing NIH-3T3 cells after 2 hours on the nanopillar electrode array. The scale bar in the lower right represents 2 µm.

To obtain nanopillars, a two-step silicon reactive-ion etching (RIE) process was used, using $SF_6(g)$ chemistry. Anisotropic etching, using 300 W RF bias power and 120 sccm (standard cubic centimeters per minute) $SF_6$ flow rate at low pressure (50-120 mTorr) to create vertical etch patterns (FIG. 1E), This was followed by isotropic etching, using high RF bias power of 500 W and 120 sccm $SF_6$ flow rate at high pressure (500-1000 mTorr) to obtain the desired undercutting (FIG. 1F). The photoresist and aluminum were then removed using an aluminum etchant—Type A (Transene Company, Inc., Danvers, Mass.) at 65° C. for 10 minutes (FIG. 1G). Different mask sets were used for nanofins and nanopillars (FIGS. 4A-4C).

Finally, a thin layer of gold was deposited using electron beam deposition technique for electrode stimulation studies.

An analogous method can be used in the preparation of nanofins.

In another method of manufacture, Focused Ion Beam (FIB) milling was used to fabricate nanofins, using a gallium imaging beam of 30 KV, 275 pA. In this method, fabrication of all the vertical lines was performed; followed by horizontal fabrication that yielded a nanofin array. Using this method, an array of 100×100 μm can take upwards of 12 hours. Nanopillars were additionally manufactured using FIB milling, but the parameters were not optimized to provide uniform 'sharp' tips and so the silicon RIE manufactured nanopillars were used in the examples described below.

Cell Culture

The nanoelectrode surface was rinsed with acetone or isopropyl alcohol and water and blown dry with compressed nitrogen. Subsequent plasma cleaning of the surface used pressures between 170-200 mTorr and DC bias of approximately 450-500 volts. To improve cell adhesion, the nanoelectrode surface was coated with collagen at a concentration of 10 μl/mL for 12 hours and then rinsed thoroughly with water. The nanopillars were incubated in media for two hours prior to cell seeding.

Three different cell lines were used: NIH-3T3, PC12 and ADSC, each of which is electrically responsive.

NIH-3T3 fibroblasts (American Type Culture Collection ('ATCC'), Manassas, Va.) are a class of cells primarily responsible for synthesizing the Extracellular Matrix (ECM) and are one of the most abundant cell lines in the body. NIH-3T3 cells were primarily used to study adhesion characteristics with the nanoelectrode arrays. These cells were cultured in Dulbecco's modified Eagle's medium (DMEM) containing 10% Fetal Bovine Serum (FBS) and 1% antibiotic/antimycotic. Cells were seeded on nanoelectrodes at a density of 5,000 cells/$cm^2$.

PC12 (ATCC) cells are derived from pheochromocytoma of rat adrenal medulla associated with the nervous system and are essentially undifferentiated neurons, which upon treatment with nerve growth factors, differentiate into neurons with extension-like dendrites and axons. PC12 cells were used to study influence of nanoelectrode topography on the cell growth and its differentiation potential. These cells were grown in RPMI supplemented with 10% heat activated horse serum, 5% calf serum and 1% penicillin and streptomycin. The PC12 cells were seeded at a density of 10,000 cells/$cm^2$ on the nanoelectrodes; to facilitate differentiation nerve growth factor (NGF) at a concentration of 50-100 ng/mL was added to the culture media.

ADSCs (ATCC) were cultured in stromal medium consisting of DMEM/Ham's F-12 medium with 10% FBS and 1% Penstrap. Two methods of neurogenic differentiation of ADSCs were compared: (1) the stromal medium was replaced by pre-induction medium (DMEM, 20% FBS and 1 nM beta-mercaptoethanol) for up to 24 hours, followed by induction medium (DMEM/2% DMSO/200 μM BHA) and (2) a two step process: (a) the stromal medium was replaced by pre-induction medium (DMEM, 20% FBS and 1 nM beta-mercaptoethanol) for up to 24 hours, followed by induction medium (DMEM/2% DMSO/200 μM BHA) for two weeks and (b) a regime electrical stimulation protocol was used to facilitate conventional induction medium based differentiation. Pulsed DC stimuli used were in the range of 100 mV/cm field strength with monophasic 100 ms square pulse and 1 Hz frequency.

Visualization of Cells on Nanoelectrodes Via Immunostaining

Cells cultured on nanoelectrodes were fixed with 4% paraformaldehyde in PBS for 15 min, washed with PBS solution three times, and then permeabilized in 0.25% Triton-X solution for 15 minutes. Before staining, all the samples were blocked using 1% BSA in PBS for one hour. Cells were then incubated with Actin green and DAPI to visualize actin and nuclei, respectively on a Spinning Disc Confocal Microscope.

Time Dynamics and Confirmation of Penetration of Nanoelectrodes in Cells Via SEM To visualize cells on nanoelectrodes, a Carl Zeiss Auriga-BU FIB FESEM Microscope (FESEM) was used. Cells were fixed overnight at 4° C. using 25% of 0.4M cacodylate buffer, 12.5% of 16% formaldehyde, 10% of 25% glutaraldehyde and water solution. The cells were then washed three times with water and dehydrated using washes comprising increasing concentrations of acetonitrile. Finally, the samples were mounted on stubs using carbon tape and sputter-coated with 5 nm of gold-palladium. The cross-section of the cell was obtained using Focused Ion Beam (FIB) on the FIB-FESEM.

Viability of Cells Seeded on Nanoelectrodes

To assess the proportion of live and dead cells of ADSCs cultured on nanoelectrodes, a live/dead cell assay kit (Molecular Probes/Life Technologies) was used, in combination with a Spinning Disc Confocal Microscope and standard established protocols.

Results and Discussion

Nanoelectrodes

Nanoelectrode arrays of 5 mm by 5 mm were prepared by the top down fabrication method disclosed above, which enabled the scalable production of silicon nanoelectrodes. The tunable geometry provided control over density, tip diameter and height of the nanoelectrodes (Table 1 and FIGS. 2A, 2B, and 2C). The density of the nanoelectrodes was controlled using the appropriate mask, while the height of the pillars was controlled during the RIE step. The tip diameter was controlled within few tens of nanometers using an optimized etching process. The sharpness of the nanopillar tip contributed to a higher probability of cell penetration. The nanofins have greatly reduced interfacial impedance and electrode resistance compared to nanopillars, while maintaining minimal cell damage.

Visualization of Cells on Nanoelectrodes Via Immunostaining

To better understand how cells responded to the nanoelectrodes, high resolution confocal microscopy was used to image NIH/3T3 cells' cytoplasm. The spacing of nanopillars contributed to improved cell-substrate interaction. Without being bound by theory, higher density nanoelectrodes may result in a "bed of nails" effect—cells may remain suspended on top of the electrodes and not conform around them. To ensure good cellular interaction, a spacing of 10 μm was chosen. Imaging showed the NIH/3T3 cells interacting with the nanoelectrodes and depicts the cytoplasm exclusion effect, where the nanoelectrodes are located. The nanoelectrodes have completely penetrated the cell. While the cytoplasmic exclusion effect could be evidence for cell membrane penetration, alternately it could mean that the cell membrane is tightly wrapped around the high aspect ratio nanoelectrodes, leading to similar cytoplasmic images without membrane penetration. To gain better insight into cell membrane conformation around the nanoelectrodes, detailed SEM imaging was undertaken.

Confirmation of Penetration of Nanoelectrodes in Cells Via SEM

SEM images of cell-nanopillar interface for NIH/3T3 cells on nanopillars at different time points were collected (FIGS. 5A-5D). NIH/3T3 cells were seeded on nanoelectrode arrays. The initially sphere-shaped cells settled onto the nanopillars (~5 min), then gradually continued to adhere to the substrate, which led to cell spreading (~30 min). The cell spreading causes an increase in the substrate contact area over time without causing any cell damage.

Figure 6A:
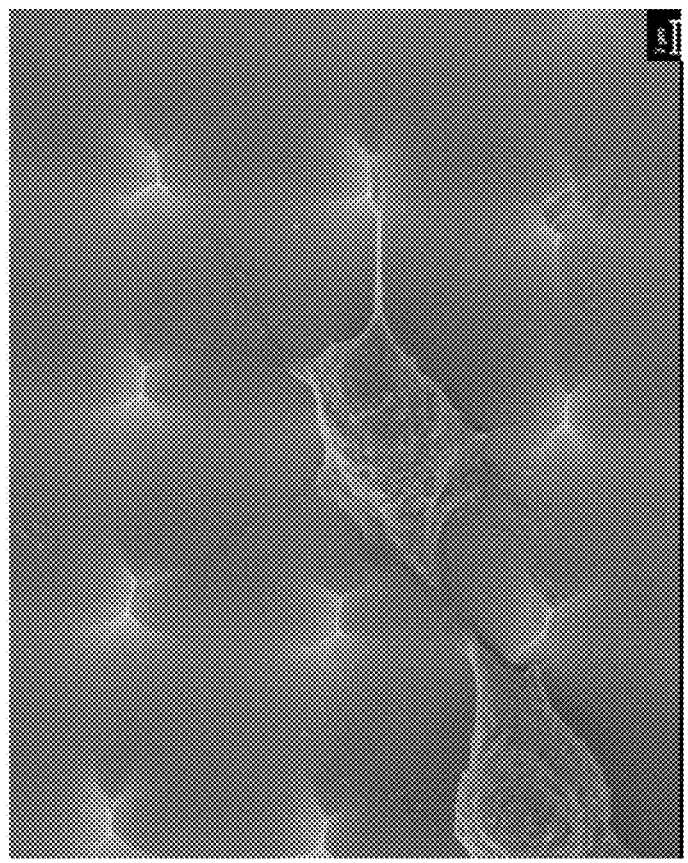
FIG. 6A is an SEM image of differentiated PC12 cells penetrated by nanofin electrodes. The scale bar in the lower right represents 2 µm.
Figure 6B:
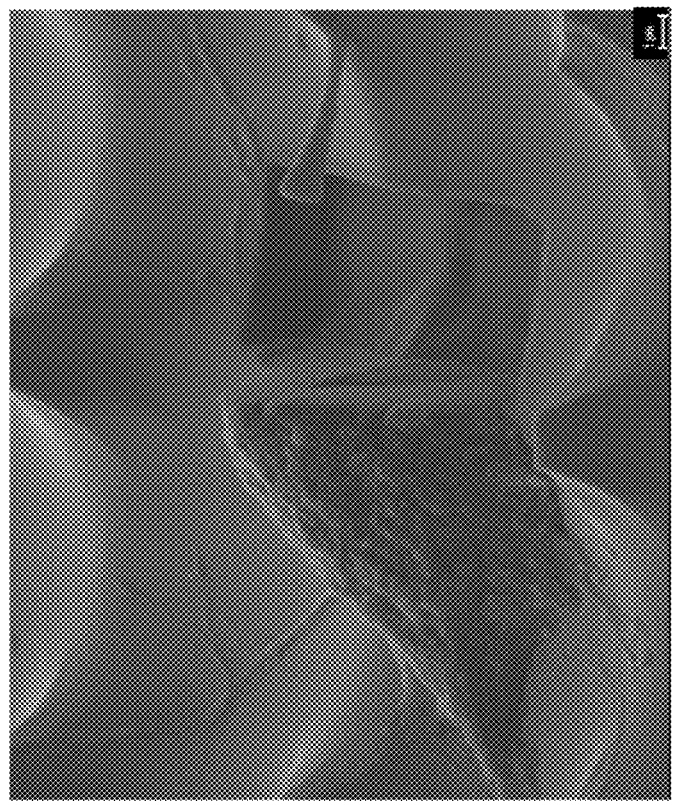
FIG. 6B is an SEM image of a PC12 cell penetrated by a nanofin electrode; the image was collected after focused ion beam (FIB) ion-milling of one half of the electrode-cell interface. The scale bar in the lower right represents 1 µm.

PC12 cells were used to study the effect of nanoelectrodes on cell differentiation. Nerve Growth Factor (NGF)-induced differentiation of PC12 cells (FIG. 6A) showed a neurite outgrowth. The nanofin-i/cell interface cross-sections were imaged following focused ion beam (FIB) milling of the interface, (FIG. 6B) and revealed that the cell completely surrounded the nanofin-i electrode. The FIB-SEM results were consistent with confocal microscopy images, which clearly showed cell membrane deformation around the nanopillars, demonstrating that the nanoelectrode penetrated the cytosol of the cell.

ADSCs cultured on nanoelectrodes and non-patterned substrates were evaluated using live/dead cell assays, which allows investigation of cell morphology. Although cell morphology may differ based on different underlying substrate patterns (nanoelectrode or non-patterned), the proportion of live cells on both nanoelectrodes and non-patterned substrate were approximately the same. Thus nanoelectrodes do not cause any loss of cell viability or function, when compared to flat or non-patterned substrates.

Differentiation in Combination Treatment

ADSCs differentiated into neural lineage using growth factors, as evaluated by a positive expression of PAX6 and Nestin, after two weeks of incubation in neural differentiation medium.

Using a combination of electrical stimulation and growth in the neural differentiation medium, ADSC differentiation was reduced to less than a week.

Example 2

Using the penetrating nanofins-i described in Example 1, the effect of electrical stimulation from a penetrating nanofin electrode was evaluated for the differentiation of ADSC, compared to controls (a) neural induction without electrical stimulation, and (b) neural induction with electrical stimulation via a plain substrate. The ADSC were prepared as disclosed above and approximately 30,000 cells were seeded per square centimeter and grown for 2-3 days at 37° C. and 5% $CO_2$, on a plain silicon substrate with gold electrodes or on a nanofin-i array.

Neural Induction

ADSCs were plated on tissue culture plates at a density of $1 \times 10^5$ cells/$cm^2$ in Neurobasal medium (ThermoFischer Scientific, Waltham, Mass.) supplemented with 93% $N_2$, 20 ng/mL epidermal growth factor (EGF) and 20 ng/mL fibroblast growth factor-2 (FGF-2). After 5-7 days, sphere formation was observed. These neurosphere-like structures were plated on poly-d-lysine-coated plates at a density of $1.5-2 \times 10^5$ cells/$cm^2$ in Neurobasal medium supplemented with 1% $N_2$, 10 ng/ml brain-derived neurotrophic factor (rhBDNF), and 1% Penicillin/Streptomycin.

Neutral Medium

ADSCs were plated on tissue culture plates at a density of $1 \times 10^5$ cells/$cm^2$ in stromal medium consisting of DMEM/Ham's F-12 medium with 10% FBS and 1% A Penstrap. The resulting neurosphere-like structures were plated on poly-d-lysine-coated plates at a density of $1.5-2 \times 10^5$ cells/$cm^2$ in Neurobasal medium supplemented with 1% $N_2$ and 1% Penicillin/Streptomycin.

Electrical Stimulation

The ADSC were kept on the substrates in an incubator, except for electrical stimulation of up to 15 minutes per day over the course of 3 or 5 days at the voltage identified in Table 2, as appropriate.

TABLE 2

Electrical Stimulation of ADSC

| Electrical Stimulation | Chemical Induction | Penetrating nanofin or plain substrate |
| --- | --- | --- |
| No | Yes (100%) | Plain substrate |
| No | Yes (100%) | Penetrating nanofin |
| Yes (50, 100, 200, or 500 mV) for 3 days | No | Plain substrate |
| Yes (50, 100, 200, or 500 mV) for 5 days | No | Plain substrate |
| Yes (100 mV) for 5 days | Yes (50%) | Plain substrate |
| Yes (100 mV) for 5 days | Yes (50%) | Penetrating nanofin |
| Yes (100 mV) for 5 days | No | Penetrating nanofin |

Immunofluorescence Studies

For confocal microscopy, cells were briefly rinsed with 1×DPBS at 37° C.; washed cells were fixed with 4% paraformaldehyde in PBS for 15 minutes at room temperature. The samples were washed three times with 1×DPBS for two minute each. Cells were than permeabilized with 0.2% Triton X-100 diluted with PBS for 15 minutes. Samples were rinsed again with 1×DPBS three times for two minute each. BLOCK with 2% BSA for 60 minutes before adding staining agents. Nuclei were stained with DAPI and F-actin was detected using phalloidin. Laser scanning confocal microscopy was performed to observe the cell spreading and cytoskeletal structure using a Carl Zeiss Axio Observer Z1, Spinning Disc Confocal Microscope (Carl Zeiss, Jena, Germany) and images were acquired at different magnifications of dry objective or 63× and 100× using an oil immersion objective.

For staining ADSCs, approximately 30,000 cells were seeded per square centimeter and grown for 2-3 days at 37° C. and 5% $CO_2$. All the media was removed, and cells were washed three times with PBS and then fixed in 2% paraformaldehyde/PBS for 5 min at room temperature. PBS and 0.5% Tween 20 was used to wash the cells three times. Cells were then incubated in blocking solution of 5% normal goat serum or bovine serum albumin for 1 hr at room temperature. Samples were then incubated with desired antibodies for 1 hr at room temperature, followed by three washes in PBS/0.5% Tween 20 and then incubation in secondary antibodies at 1:100 dilutions for 45 min at room temperature. After washing three time with PBS/0.5% Tween 20, the cells were imaged using Carl Zeiss Axio Observer Z1, Spinning Disc Confocal Microscope (Carl Zeiss, Germany).

To stain cells after neural induction, initially all the media from the cells was removed and the cells were washed with PBS. Cells were then fixed with 4% paraformaldehyde for 15 min at room temperature and then rinsed three times with PBS. The cells were then blocked in PBS/5% bovine serum albumin/0.1% Triton X-100 for 30 minutes. Cells were then incubated with primary antibodies at 4° C. overnight and then with secondary antibody for 1 hr at room temperature.

Serum Free Induction

After 2 weeks of growth in 100% neural induction media, the cultured ADSCs showed an increase in decrease in ADSC markers (CD 45, CD 44, and CD 29) and an increase in NSC markers (Vimentin, Nestin and PAX 6).

Electrical Stimulation on Plain Substrate

To compare the effect of electrical stimulation on the differentiation of ADSC, ADSCs that had been cultured in a medium lacking any growth factors or chemical inductors were exposed to pulsed DC stimuli with monophasic 100 ms square pulse at varying field strengths: 50 mV, 100 mV, 200 mV, or 500 mV for 15 minutes per day for 3 days. After 3 days of treatment, no significant loss of cell viability was noticed. The ADSC markers showed decreased expression, while the NSC markers showed increased expression, compared to control (no electrical stimulation).

Electrical Stimulation Supplementing 50% Neural Induction Medium

ADSCs cultured in 50% of the neural induction medium were exposed to pulsed DC stimuli with monophasic 100 ms square pulse of 100 mV/cm field strength for 15 minutes per day for 5 days. After 5 days of treatment, no significant loss of cell viability was noticed. The ADSC markers showed decreased expression, while the NSC markers showed increased expression, compared to controls: (a) electrical stimulation on plain substrate with 50% neural induction medium and (b) growth on plain substrate with 50% neural induction medium. Morphological changes, including shrinking of the cell body and sprouting of neuronal extensions, were also observed, similar to the changes observed in cells grown in 100% induction medium.

Electrical Stimulation Only

ADSCs cultured in a medium lacking any growth factors or chemical inductors were exposed to pulsed DC stimuli with monophasic 100 ms square pulse of 100 mV/cm field strength for 15 minutes per day for 5 days. After 5 days of treatment, no significant loss of cell viability was noticed. No consistent morphological changes were observed, but some neuron extensions were observed. The ADSC markers, CD29 and CD44, showed decreased expression, while the NSC markers, Vimentin, Nestin, and PAX 6, showed increased expression, compared to controls: (a) electrical stimulation on plain substrate with 50% neural induction medium and (b) growth on plain substrate with 50% neural induction medium. Although not measured in this experiment, other ADSC markers, including CD9, CD10, CD13, CD49, CD54, CD55, CD59, CD73, CD90, CD105, CD106, CD146, CD166, ASMA, Collagen-1, Endomucin, and Fibronectin, would also show decreased expression, consistent with differentiation of ADSC to neural lineage.

The expression of mature neuronal markers, MAP2 and β-tubulin III, will show increases in expression of the ADSC undergoing electrical stimulation alone via penetrating nanoelectrodes.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of modulating an adipose-derived stem cell having a cytosol, comprising exposing said cytosol to electrical stimulation, thereby modulating the cell, wherein a nanoelectrode provides said electrical stimulation.

2. The method of claim 1, wherein said modulating comprises differentiating the cell to a neural lineage.

3. The method of claim 2, wherein said differentiating to neural lineage is characterized by an increase in one or more neural stem cell markers.

4. The method of claim 3, wherein said markers include one or more of Nestin and PAX6.

5. The method of claim 1, wherein said nanoelectrode penetrates the cell and is in physical contact with the cytosol.

6. The method of claim 5, wherein said electrical stimulation is pulsed direct current at 100 mV/cm field strength.

7. The method of claim 6, wherein the stimulation is a monophasic 100 ms square pulse at 1 Hz frequency.

8. The method of claim 1, wherein said cell is exposed to a growth factor or chemical agent, wherein said modulating comprises differentiating the cell to a neural lineage and said differentiating occurs in a shorter time compared to differentiating in the absence of said electrical stimulation.

9. The method of claim 1, wherein said cell is not exposed to a growth factor or chemical agent during said modulation.

10. The method of claim 1, wherein said nanoelectrode is a nanofin having a width of no more than about 100 nm and a length of no more than about 7.5 μm.

11. The method of claim 1, wherein said nanoelectrode is a conical nanopillar having a radius no larger than about 300 nm.

12. A method for differentiating an adipose-derived stem cell to a neural lineage comprising applying electrical stimulation to the cytosol of the stem cell, wherein a nanoelectrode provides said electrical stimulation to the cytosol.

13. The method of claim 12, wherein said nanoelectrode penetrates the cell and is in physical contact with the cytosol.

14. The method of claim 13, wherein said electrical stimulation is pulsed direct current at 100 mV/cm field strength.

15. The method of claim 12, wherein said nanoelectrode is a conical nanopillar having a radius no larger than about 300 nm.

16. The method of claim 12, wherein said nanoelectrode is a nanofin having a width of no more than about 100 nm and a length of no more than about 7.5 μm.

* * * * *